United States Patent [19]

Mayer et al.

[11] 4,006,239

[45] Feb. 1, 1977

[54] BENZOIC ACID AMIDES FOR MYCOBACTERIUM INFECTIONS

[75] Inventors: Karl Heinrich Mayer, Opladen-Quettingen; Hans-Joachim Kabbe, Leverkusen; Hinrich Otten, Wuppertal-Elberfeld, all of Germany

[73] Assignee: Bayer Aktiengesellschaft, Germany

[22] Filed: Apr. 2, 1975

[21] Appl. No.: 564,224

[30] Foreign Application Priority Data

Apr. 11, 1974 Germany .......................... 2417763

[52] U.S. Cl. ............................................. 424/263
[51] Int. Cl.[2] ........................................ A61K 31/44
[58] Field of Search ............ 260/295 AM; 424/263

[56] References Cited

UNITED STATES PATENTS 2,870,156  1/1959  Perron et al. ............. 260/295 AM
3,367,940  2/1968  Hotten ....................... 260/295 AM
3,455,940  7/1969  Stecker ...................... 260/295 AM
3,676,447  7/1972  Skinner et al. ............. 260/295 AM

*Primary Examiner*—Norman A. Drezin

[57] ABSTRACT

Benzoic acid amides characterized by the presence of a hydroxy or amino substituent in the phenyl ring, or an alkylated or acylated derivative thereof and by a heterocyclic group connected to the amide nitrogen atom through a hydrocarbon chain are antibacterial agents and in particular anti-tuberculosis agents. The compounds, of which N-[pyridyl-(2)-methyl]-2-hydroxybenzoic acid amide is a typical embodiment, are prepared by the reaction of an appropriately substituted benzoic acid, or derivative thereof, with an appropriate amine.

14 Claims, No Drawings

BENZOIC ACID AMIDES FOR MYCOBACTERIUM INFECTIONS

DETAILED DESCRIPTION

The present invention pertains to novel benzoic acid amides, to processes for their preparation and their use as antimicrobial substances, especially as anti-tuberculosis agents.

While some fourteen medicaments active against tuberculosis are known, it has not yet proved possible to develop a reliable scheme of chemotherapy. Instead, it has always been necessary to carry out a multiple therapy; i.e., three or more anti-tuberculosis active compounds of different mechanisms of action are combined, in accordance with the particular circumstances of the patient. The fourteen types of anti-tuberculosis active compounds clinically in use can be divided into nine groups on the basis of the parallel resistance which in part exists between them, from which a three drug combination scheme, or in cases presenting special problems up to five drug combination scheme, for the individual patient can be composed. Since the commercially available agents against tuberculosis show side effects in up to 30% of the patients, it is understandable that carrying out a complete tuberculosis therapy also presents very great problems in relation to the tolerance of the medicaments. As a result, there is a demand for new agents against tuberculosis which either display new mechanisms of action against mycobacteria or display better tolerance; see, e.g. E. Freerksen in R. Hauben: Blasige Lungenkranheiten; poststenotisches Bronchosyndrom; Alveolare Proteinose; Tuberkulostatika zweiter Ordnung [Vesicular Diseases of the Lungs; Poststenotic Bronchosyndrome; Alveolar Proteinosis; Second Order Tuberculostatic Agents], Georg Thieme Verlag, Stuttgart, 1968, 141 – 152.

The present invention pertains to benzoic acid amides of the formula:

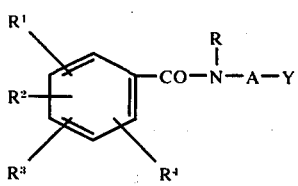

wherein R is hydrogen, lower alkyl, phenyl (lower alkyl) or pyridyl (lower alkyl);

each of $R^1$, $R^2$, $R^3$ and $R^4$ is independently selected from the group consisting of hydrogen; hydroxy; lower alkoxy; lower alkanoyloxy; amino; lower alkylamino; di(lower alkyl)amino; lower alkanoylamido; benzamido; phenyl(lower alkanoyl)amido; carbo(lower alkoxy)amino; dicarbonylimido wherein each carbonyl group is bound to lower alkylene, phenyl or phenyl(lower alkylene); halogeno; lower alkyl; phenyl(lower alkyl); nitro; trifluoromethyl; cyano; lower alkylsulfonyl; carboxy and carbo(lower alkoxy), provided at least one of $R^1$, $R^2$, $R^3$ and $R^4$ is hydroxy, lower alkoxy, lower alkanoyloxy, amino, lower alkylamino, di(lower alkyl)amino, lower alkanoylamino, benzamido, phenyl(lower alkanoyl)amido, carbo(lower alkoxy)amino, or dicarbonylimido;

A is alkylene of 1 to 6 carbon atoms, unsubstituted or substituted by phenyl; and Y is a saturated or unsaturated heterocyclic system having from 5 to 10 ring members, one to three of which are hetero-atoms independently selected from the group consisting of oxygen, nitrogen and sulfur and the remainder of which are carbon, said heterocyclic system being unsubstituted or substituted by a member selected from the group consisting of lower alkyl, halogeno, lower alkoxy, nitro, amino, or trifluoromethyl;

b. the pharmaceutically acceptable acid addition salts of said benzoic acid amides which bear at least one basic nitrogen atom or amino group in the substituents R, $R^1$, $R^2$, $R^3$, $R^4$ and Y; and c. a pharmaceutically acceptable alkali metal, alkaline earth metal or amine salt of said benzoic acid amides which bear a free carboxy group as one of the substituents $R^1$, $R^2$, $R^3$ and $R^4$.

The benzoic acid amides of Formula I and their salts have anti-tuberculosis properties. Chemically these compounds are characterized (a.) by at least one hydroxy or amino group, or an alkylated or acylated derivative thereof, in the aromatic ring of the benzoic acid amide, optionally with further substitution in this ring, and (b.) a heterocyclic group (Y) linked to the nitrogen atom of the amide through a hydrocarbon chain (A).

In one embodiment of the invention, the heterocyclic ring system is tetrahydrofuryl, dihydropyranyl, thienyl, pyrrolyl, pyrazolyl, imadazolyl, triazolyl, oxazolyl, isoxazolyl, thiazolyl, pyridyl, pyrimidyl, pyrrolidinyl, piperazinyl, pyrazinyl, indazolyl, azepinyl, quinolyl or isoquinolyl.

In a further embodiment of the invention, the heterocyclic system of Y contains one or two nitrogen atoms as the only hetero-atoms and is either an unsaturated monocyclic system of 5 or 6 ring members or a fused benzo system of 9 or 10 ring members.

In still a further embodiment of the intention, the heterocyclic system of Y is pyrrolyl, pyridyl, pyrimidyl, quinolyl, isoquinolyl, pyrazinyl or indazolyl.

In another embodiment of the invention, the heterocyclic system of Y is tetrahydrofuryl or dihydropyranyl.

In another embodiment the hydrocarbon chain A is preferably methylene, ethylene, propylene or benzylidene.

In another preferred embodiment, one of $R^1$, $R^2$ and $R^3$ is hydroxy, alkoxy of 1 to 4 carbon atoms or amino.

In another embodiment, the nitrogen atom of the amide is further unsubstituted (R=H) or substituted so that R is methyl, ethyl, benzyl or pyridylmethyl.

A particularly preferred subgroup are those compounds wherein each of $R^1$, $R^2$ and $R^3$ is selected from the group consisting of hydrogen, hydroxy, alkoxy of 1 to 4 carbon atoms, alkanoyloxy of 2 to 4 carbon atoms, amino, alkanoylamido of 2 to 4 carbon atoms, carbalkoxyamido of 3 to 5 carbon atoms, chloro, bromo, alkyl of 1 to 4 carbon atoms, nitro, trifluoromethyl and cyano provided that one of $R^1$, $R^2$ and $R^3$ is hydroxy, alkoxy, alkanoyloxy, amino, alkanoylamido or carbalkoxyamido;

$R^4$ is hydrogen;

A is methylene, ethylene, propylene or benzylidene; and

Y is tetrahydrofuryl, dihydripyranyl, pyrrolyl, pyridyl, methylpyridyl, pyrazinyl, quinolyl, isoquinolyl or indazolyl.

Of these compounds the pyridyl-(2)-methyl derivatives are especially valuable.

The invention also dihydropyranyl, a method of preparing the benzoic acid amides of Formula I and their salts which comprises
a. reacting an acid halide of the formula:

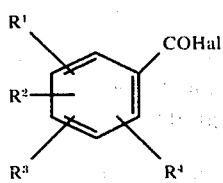 (II)

in which $R^1$, $R^2$, $R^3$ and $R^4$ are as defined above; and

Hal represents a chlorine or bromine atom with an amine of the formula:

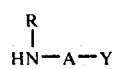 (III)

in which R, A and Y are as defined above, optionally in the presence of acid-binding agents;
b. reacting a carboxylic acid of the formula:

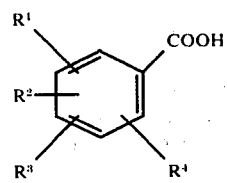 (IV)

in which $R^1$, $R^2$, $R^3$ and $R^4$ are as defined above, with an amine of Formula III in the presence of an agent which split off water;

c. reacting a carboxylic acid ester of the formula:

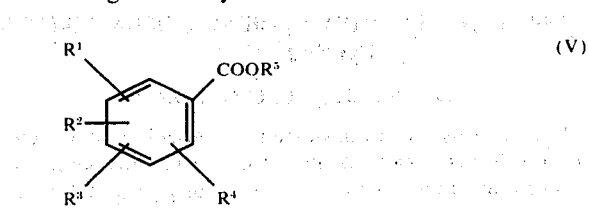 (V)

in which $R^1$, $R^2$, $R^3$ and $R^4$ are as defined above; and $R^5$ is alkyl or aryl, with an amine of Formula III, with elimination of $R^5OH$; or
d. reacting an anhydride of the formula:

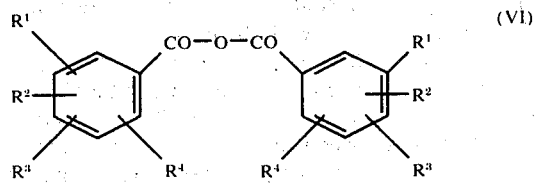 (VI)

in which $R^1$, $R^2$, $R^3$ and $R^4$ are as defined above, with an amine of Formula III.

In addition to the foregoing processes, one can also effect various interconversions with the final compounds. Alkoxycarbonyl groups can be converted into carboxyl or aminocarbonyl groups. Nitro groups can be reduced to amino groups. The hydroxyl or amino groups present in the compounds of Formula I can be alkylated or acylated. Where appropriate, the compounds obtained can be converted into the salts.

If 2-methoxybenzoyl chloride and 2-amino-methyl-pyridine (process variant a), 4-dimethylaminobenzoic acid and 2-aminomethylpyridine (process variant b), salicyclic acid phenyl ester and 3-aminomethylquinoline (process variant c) or 4-methoxybenzoic anhydride and 2-(α-amino-ethyl)-pyridine (process variant d) are used as illustrative starting materials, the course of these reactions can be represented as follows:

a)
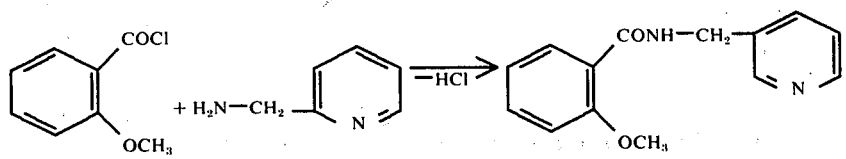

b)
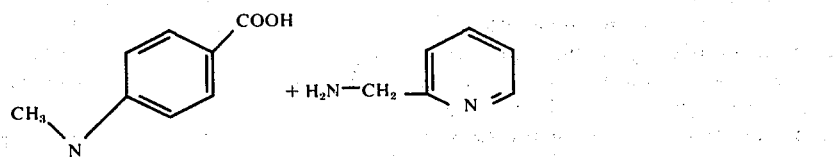

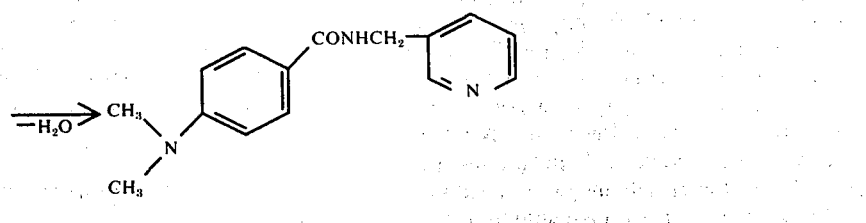

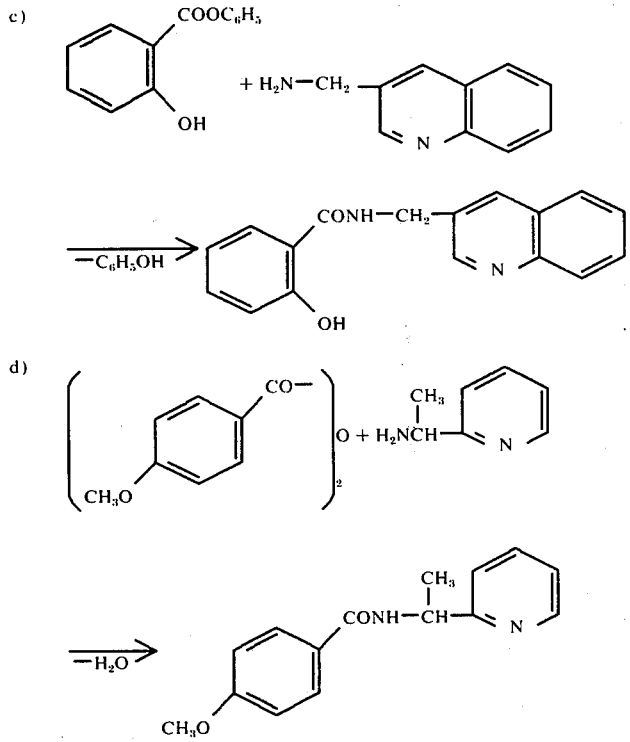

An example of an optional subsequent reaction is the reduction of a nitro group:

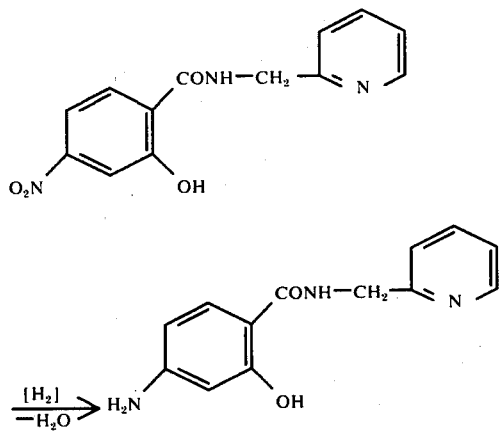

Lower alkyl groups for R, $R^1$, $R^2$ and $R^5$ in the above formulas, for $R^6$ mentioned later, and for the optional substituents on Y are straight or branched monovalent hydrocarbon chains with 1 to 6, especially 1 to 4, carbon atoms, as for example methyl, ethyl, n- and i-propyl and n-, i-and t-butyl.

Lower alkoxy groups are such lower alkyl groups with 1 to 6, especially 1 to 4, carbon atoms joined through an ethereal oxygen atom. Methoxy, ethoxy, n- and i-propoxy and n-, i- and t-butoxy can be mentioned as examples.

Lower alkylene groups embraced by A are those straight and branched chains having 1 to 6 carbon atoms with from 1 to 3 carbon atoms between the valence bonds. Methylene, ethylene, propylene, methylmethylene, ethylidene, 1-or 2-methylethylene, phenylmethylene and 2-pyridylmethylene may be mentioned as examples.

Lower alkylsulphonyl groups contain 1 to 6, especially 1 or 2, carbon atoms. Methylsulphonyl, ethylsulphonyl, n-and i-propylsulphonyl and n-, i- and t-butylsulphonyl may be mentioned as examples.

Preferred alkoxycarbonyl groups [carbo(lower alkoxy)] contain 1 to 6, especially 1 or 2, carbon atoms in the alkoxy part. Methoxycarbonyl, ethoxycarbonyl, n- and i-propoxycarbonyl and n-, i- and t-butoxycarbonyl may be mentioned as examples.

Preferred aralkyl groups for R, $R^1$ and $R^2$, and $R^6$, mentioned subsequently, contain 6 or 10, especially 6, carbon atoms in the aryl part and 1 to 6, preferably 1 to 4 and especially 1 or 2, carbon atoms in the alkyl part, which part can be straight or branched chain. Benzyl and phenylethyl can be mentioned as examples.

Acyl groups for the radical $R^1$ will contain 1 to 8, preferably 1 to 5, carbon atoms. Examples include acetoxy, propionyloxy, isopropionyloxy, butyroyloxy, isobutyroyloxy, pivaloyloxy and benzoy. Phthalimino, succinimino and glutarimino may be mentioned as the diacylamino group in $R^1$.

Preferred aryl groups for the radicals R, $R^5$, $R^6$, mentioned later, and the optional substituent on Y contain 6 to 10 carbon atoms in the aryl part. Phenyl and naphthyl can be mentioned as examples.

Y represents a 5- to 10-membered, (usually 5-membered or 6-membered when monocyclic) saturated or unsaturated heterocyclic ring system with 1 to 3, usually 1 or 2, identical or different hetero atoms, such as oxygen, sulphur, and/or nitrogen. The heterocyclic radical can contain one or more, preferably 1 to 3, especially 1 or 2, identical or different substituents. If aryl radicals such as phenyl are present as substituents, these can in turn be substituted by 1 to 3, preferably 1 or 2, halogen atoms, such as chlorine, fluorine or bromine, preferably chlorine and bromine, alkyl groups with 1 to 4 carbon atoms, preferably methyl or ethyl, alkoxy groups with 1 to 4 carbon atoms, preferably methoxy or ethoxy, nitro, cyano and/or trifluoromethyl radicals. The heterocyclic radical can also carry a fused benzo ring which can be substituted in the same way as the aryl radical. The following are examples of such heterocyclic ring systems: furyl, tetrahydrofuryl, 5-methylfuryl, 5-(3',4'-dichlorophenyl)-furyl, thienyl, pyrrolyl, pyrrolidinyl, imidazolyl, pyrazolyl, triazolyl, oxazolyl, isoxazolyl, thiazolyl, 4-methylthiazolyl, isothiazolyl, oxadiazolyl, pyranyl, dihydropyranyl, pyridyl, 2,6-dimethylpyridinyl, pyridazyl, pyrimidinyl, pyrazinyl, piperazinyl, oxazinyl, isoxazinyl, azepinyl, oxepinyl, thiepinyl, indolyl, benzimidazolyl, benzoxazolyl, quinolyl, tetrahydroquinolyl, isoquinolyl, quinazolyl, quinoxalyl and cinnolyl.

Halogeno denotes fluoro, chloro, bromo and iodo, preferably fluoro, chloro and bromo and especially chloro and bromo.

The acids of Formula IV used as starting materials are known in most cases and can be converted in accordance with known methods into the acid halides II, the esters V and the anhydrides VI and VII. The following may be mentioned as examples: 2-hydroxybenzoic acid, 3-hydroxybenzoic acid, 4-hydroxybenzoic acid, 2-methoxybenzoic acid, 3-methoxybenzoic acid, 4-methoxybenzoic acid, 2-hydroxy-5-nitrobenzoic acid, 2-hydroxy-4-nitro-benzoic acid, 2-hydroxy-3-nitro-benzoic acid, 2-hydroxy-5-chloro-benzoic acid, 2-hydroxy-5-cyano-benzoic acid, 2-hydroxy-3-methyl-benzoic acid, 2-methoxy-4-methyl-benzoic acid, 2-methoxy-5-chloro-benzoic acid, 2-hydroxy-5-methylsulphonyl-benzoic acid, 2-carbo-methoxy-5-hydroxy-benzoic acid, 2-carboxy-4-methoxy-benzoic acid, 3-hydroxy-4-dimethylamino-benzoic acid, 3-phthalimido-5-nitrobenzoic acid, 2-acetoxybenzoic acid, 2-propionyl-oxybenzoic acid, 2-pivaloyl-oxybenzoic acid, 2-benzoyl-oxy-benzoic acid, 3-butyroyloxybenzoic acid, 3-benzoyloxybenzoic acid, 4-isopropionyloxybenzoic acid, 4-acetoxy-3-trifluoromethyl-benzoic acid, 2-hydroxy-4-aminobenzoic acid, 2-acetoxy-4-acetylaminobenzoic acid, 2-butyroyloxy-4-butyroylaminobenzoic acid, 2-benzoyloxy-4-benzoylaminobenzoic acid, 2-methoxy-4-aminobenzoic acid, 2-ethoxy-4-acetylaminobenzoic acid, 2-hydroxy-5-aminobenzoic acid, 2-hydroxy-3-aminobenzoic acid, 3,4,5-trimethoxybenzoic acid, 3,5-dinitro-2-hydroxybenzoic acid, 5-benzyl-2-hydroxybenzoic acid, 2-hydroxy-3-amino-5-nitrobenzoic acid, 2-hydroxy-3-cyano-5-nitrobenzoic acid, 2-hydroxy-3-nitro-5-aminobenzoic acid, 2-hydroxy-3-nitro-5-cyanobenzoic acid, 2-hydroxy-4,6-dimethyl-benzoic acid, 2-hydroxy-3-methyl-5-chlorobenzoic acid, 2-hydroxy-3-amino-5-nitrobenzoic acid, 2-methoxy-3-cyano-5-nitrobenzoic acid, 2-acetoxy-3-nitro-5-aminobenzoic acid, 2-hydroxy-3-methyl-5-cyanobenzoic acid as well as the corresponding anhydrides, chlorides, bromides and methyl, ethyl, n- and i-propyl and n-, i- and t-butyl esters.

The amines III used as starting materials are also known or can be prepared according to generally known methods, for example by reaction of halogenoalkylheterocyclic compounds of the formula:

, Hal-A-Y (VIII)

in which

Hal is bromine, chlorine or iodine and

A and Y are as defined above, with amines of the formula:

, R-NH$_2$ (IX)

in which

, R is as defined above, or by hydrogenation of nitriles of the formula:

, Y-CN (X)

in which

, Y is as defined above, or by hydrogenation of carbonyl compounds of the formulas XI and XII:

, Y-CHO (XI)

, Y-CO-R$^6$ (XII)

in which

R$^6$ is alkyl, aryl or aralkyl, and

Y is as defined above, in the presence of ammonia.

The following may be mentioned as examples of amines of the formula III: α-, β- and γ-aminomethylpyridine, α-, β- and γ-aminomethylquinoline, 1-amino-2-(α-pyridyl)-ethane, 1-amino-2-(β-pyridyl)-ethane, 1-amino-2-(γ-pyridyl)-ethane, 1-amino-1-(α-pyridyl)-ethane, 1-amino-1-(β-pyridyl)-ethane, 1-amino-1-(γ-pyridyl)-ethane, 1-amino-2-(γ-pyridyl)-propane, 2-aminomethyl-6-methyl-pyridine, 3-aminomethyl-1,2,3,4-tetrahydroquinoline, 1-amino-methyl-isoquinoline, 2-amino-methylpyrimidine, 4-amino-methylpyrimidine, 4-amino-methyl-5-methylpyrimidine, 4-(α-amino-ethyl)-pyrimidine, β-aminosulpholane, N-benzyl-N-α-pyridylmethylamine, N-ethyl-N-α-pyridylmethylamine, α-aminomethylfurane, α-(2-amino-ethyl)-furance, α-(1-aminoethyl)-furance, α-pyridyl-phenyl-methylamine, N-di-(α-pyridyl)-amine, N-di-(γ-pyridyl)-amine, γ-(N-pyrrolyl)-propylamine, α-aminomethyl-tetrahydrofurane, α-amino-methyldihydropyrane, β-(2-aminoethyl)-indole, 2-aminomethyl-5-methylfurance, 2-aminomethylbenzimidazole, 2-aminomethyl-5-(3,4-dichlorophenyl)-furance, 2-(β-aminoethyl)-4-methylthiazole, 1-(β-aminoethyl)-triazole-(1,2,3), N-methyl-N'-aminopropylpiperazine, N-aminoethylthiomorpholinedioxide, N-aminopropylmorpholine, α-aminomethylpyrazine, 3-aminomethylindazole, aminoethylpyrrolidine, N-aminopropylindoline, N-aminomethylindoline, N-aminopropylhexamethyleneimine, α-aminomethylbenzodioxane-(1,4), 4-amino-methyl-cinnoline and 4-amino-methyl-quinazoline.

Diluents which can be used in process variants a) to d) are generally inert organic solvents. These include hydrocarbons such as benzene, toluene and xylene, halogenohydrocarbons such as chloroform, carbon tetrachloride, chlorobenzene and dichlorobenzene, ethers such as diethyl ether, tetrahydrofuran and dioxane, amides such as dimethylformamide, esters such as ethyl acetate, nitriles such as acetonitrile and propionitrile and ketones such as methyl isobutyl ketone.

All customary acid-binding agents can be used as acid binders in process variant a). They include the alkali metal hydroxides such as sodium hydroxide or potassium hydroxide, alkali metal carbonates, such as sodium carbonate and potassium carbonate, alkali metal bicarbonates such as sodium bicarbonate and potassium bicarbonate and organic bases for example organic amines such as pyridine, triethylamine and tributylamine.

In process variant b), it is possible to utilize any of the customary agents which split off water and which are employed for the preparation of amides from acids and amines, as for example carbodiimides such as dicyclohexylcarbodiimide or inorganic acid chlorides, such as phosphorus oxychloride or thionyl chloride.

Process variant c) can optionally also be carried out without diluents.

In all process variants (a) to (d) the reaction temperatures can be varied within a considerable range. In the case of the process variants mentioned under a), b) and d), the reaction is usually carried out at between about −20° C and +100° C, preferably between 0° C and +50° C. Process variant c) in general requires higher temperatures, usually between about 20° C and 250° C and preferably 100° C to 200° C.

The reactions can be carried out under normal pressure, especially process variants a) and b), and also under elevated pressure as for example in the case of process variant c).

In carrying out the process according to the invention, the particular starting materials of Formulas II, IV, V, VI and VII and those of Formula III are preferably reacted in the molar ratio of 1.2:1 to 1:1.2, but in the case of very valuable starting materials it is, for example, also possible to choose molar ratios from 5:1 to 1:5 to achieve good yields. The molar ratios can thus vary within very wide ranges without having a particular adverse influence on the result. The acid binders in process variant a) are preferably employed in a molar equivalent amount, that is to say in an amount sufficient to bind the acid produced. However, in some cases it can be advisable to employ a smaller amount, or preferably a larger amount, of acid-binder.

If the compounds of Formula I contain alkoxycarbonyl groups, these can be converted into carboxyl or aminocarbonyl groups in accordance with generally known methods. Alkoxycarbonyl groups can, for example, be converted into carboxyl groups with alkalis such as sodium hydroxide, in aqueous alcoholic solution at room temperature or elevated temperature.

If the compounds of Formula I contain nitro groups, these can be reduced to amino groups in accordance with generally known methods. The hydroxyl or amino groups contained in the compounds of Formula I can be alkylated or acylated in accordance with known methods. The compounds according to the invention are isolated and purified if desired, in accordance with generally customary methods.

The carboxylic acid amides according to the invention can, if they contain a basic nitrogen atom in an amino substituent or heterocyclic ring or an acidic substituent, also be used in the form of their salts, with acids or bases, respectively. As examples of such acids forming acid additions salts there may be mentioned sulphonic acids such as toluenesulphonic acid, naphthalenesulphonic acid and naphthalenedisulphonic acid, carboxylic acids such as acetic acid, benzoic acid, lactic acid, citric acid and hydroxynapthoic acid and hydrogen halide acids such as hydrochloric acid and hydrobromic acid. As examples of bases suitable for forming salts they may be mentioned alkali metal bases such as sodium hydroxide solution and potassium hydroxide, alkaline earth metal bases, and organic amines such as dicyclohexylamine, triethylamine and diethanolamine. The compounds of Formula I can be converted into the salts in accordance with generally customary methods. The hydrohalides of the compounds of Formula I are also obtained if process variant a) is followed and no acid-binding agent is added. The salts are isolated and purified in accordance with generally customary methods.

The following can be mentioned individually as new active compounds: N-(furyl-(2)-methyl)-2-hydroxy-benzoic acid amide, N-(5-methyl-furyl-(2)-methyl)-N-methyl-3-hydroxy-benzoic acid amide, N-(5-(3',4'-dichlorophenyl)-furyl-(2)-methyl)-2-hydroxy-benzoic acid amide, N-(furyl-(2)-1,2-ethyl)-3-hydroxy-benzoic acid amide, N-(furyl-(2)-1,1-ethyl)-3-hydroxybenzoic acid amide, N-(tetrahydro-furyl-(2)-methyl)-2-hydroxy-benzoic acid amide, N-(thienyl-(2)-methyl)-3,5-dihydroxy-benzoic acid amide, N-(pyrrolyl-(1)-1,3-propyl)-3-nitro-5-hydroxy-benzoic acid amide, N-(tetrahydro-pyrrolyl-(1)-methyl)-3,4,5-trimethoxy-benzoic acid amide, N-(imidazolyl-(2)-1,2-propyl)-2-hydroxy-benzoic acid amide, N-(pyrazolyl-(3)-2,1-propyl)-4-hydroxy-benzoic acid amide, N-(1,2,3-triazolyl-(1)-1,2-ethyl)-3-hydroxy-benzoic acid amide, N-(oxazolyl-(2)-methyl)-2-methoxy-benzoic acid amide, N-(isoxazolyl-(3)-methyl)-3-methoxy-benzoic acid amide, N-(4-methyl-thiazolyl-(2)-1,2-ethyl)-2,4-dimethoxy-benzoic acid amide, N-($\Delta^2$-di-hydro-pyranyl-(6)-methyl)-4-methoxy-benzoic acid amide, N-(tetrahydro-pyrazinyl-(1)-1,3-propyl)-3-hydroxy-5methyl-benzoic acid amide, N-(pyridyl-(2)-methyl)-2,6-dihydroxybenzoic acid amide, N-(pyridyl-(2)-methyl)-3-hydroxy-4-methoxy-benzoic acid amide, N-(pyridyl-(2)-methyl)-2-hydroxy-3-methoxy-benzoic acid amide, N-(pyridyl-(2)-methyl)-3-carboxy-5-phthalimido-benzoic acid amide, N-(pyridyl-(2)-methyl)-2-hydroxy-5-butyl-benzoic acid amide, N-(pyridyl-(2)-methyl)-3-nitro-5-succinimido-benzoic acid amide, N-(pyridyl-(2)-methyl)-5-methoxycarbonyl-3-methoxy-benzoic acid amide, N-(pyridyl-(2)-methyl)-N-benzyl-2-hydroxy-benzoic acid amide, N-(pyridyl-(2)-methyl)-N-ethyl-4-methoxy-benzoic acid amide, N,N-bis-(pyridyl-(2)-methyl)-3,5-diamino-benzoic acid amide, N-(pyridyl-(2)-1,2-ethyl)-3,5-diacetylamino-benzoic acid amide, N-(pyridyl-(2)-1,1-ethyl)-3-nitro-5-methoxy-benzoic acid amide, N-(pyridyl-(2)-1,-benzyl)-2-hydroxy-5-chloro-benzoic acid amide, N-(6-methyl-pyridyl-(2)-methyl)-2-acetoxy-benzoic acid amide, N-(pyridyl-(3)-methyl)-4-isovaleroyloxy-benzoic acid amide, N-(pyridyl-(4)-methyl)-2-hydroxy-5-amino-benzoic acid amide, N-(pyridyl-(4)-methyl)-2-hydroxy-4-amino benzoic acid amide, N-(quinolyl-(2)-methyl)-2-hydroxy-3,5-dinitro-benzoic acid amide, N-(quinolyl-(3)-methyl)-3-hydroxy-4-trifluoromethyl-benzoic acid amide, N-(tetrahydro-quinolyl-(2)-methyl)-2-butoxy-5-benzyl-benzoic acid amide, N-($\Delta^2$-dihydro-quinolyl-(3)-1,2-ethyl)-3-amino-5-dimethylamino-carbonyl-benzoic acid amide, N-(benzimidazole-(2)-methyl)-2-isopentyloxy-benzoic acid amide, N-(pyridazyl-(3)-methyl)-2-butoxy-benzoic acid amide, N-(pyrimidyl-(2)-methyl)-2-pentoxy-benzoic acid amide, N-(pyrazinyl-(2)-1,3-propyl)-2,4-diamino-benzoic acid amide, N-(4-methyl-tetrahydro-pyrazinyl-(1)-methyl)-2-hydroxy-5-butyl-sulphonyl-benzoic acid amide, N-(tetrahydro-oxazinyl-(4)-1,3-propyl)-2-ethoxy-5-pentyl-benzoic acid amide, N-(tetrahydro-thiazinyl-1,1-dioxide-(4)-methyl)-2,4-diacetoxy-benzoic acid amide, N-(azepinyl-(2)-methyl)-2-hydroxy-5-chloro-benzoic acid amide, N-(indolyl-(3)-1,3-propyl)-3-ethoxy-benzoic acid amide, N-(indazolyl-(3)-methyl)-2-hydroxy-3-nitro-benzoic acid amide, N-(benzthiazolyl-(2)-methyl)-2-methoxy-4-nitro-benzoic acid amide, N-(quinoxalyl-(2)-methyl)-2-acetoxy-3-methyl-benzoic acid amide, N-(pyridyl-(2)-methyl)-2-amino-benzoic acid amide, N-(pyridyl-(2)-methyl)-3-amino-5-nitro-benzoic acid amide, N-(pyridyl-(2)-methyl)-4-aminobenzoic acid amide, N-(pyridyl-(2)-methyl)-2-trifluoromethyl-4-dimethylamino-benzoic acid amide, N-(pyridyl-(2)-methyl)-3-trifluoromethyl-5-butyroylamino-benzoic acid amide, N-(pyridyl-(2)-methyl)-4-benzoylamino-benzoic acid amide, N-(pyridyl-(2)-methyl)-3-cyano-5-amino-benzoic acid amide, N-(pyridyl-(2)-methyl)-3-methoxycarbonyl-5-ethylamino-benzoic acid amide, N-(pyridyl-(2)-methyl)-2-carboxy-4-hydroxy-benzoic acid amide, N-(pyridyl-(2)-methyl)-2-nitro-4-diethylamino-benzoic acid amide, N-(pyridyl-(2)-methyl)-2-methoxy-4-methylsulphonylbenzoic acid amide, N-(pyridyl-(2)-methyl)-5-bromo-2-hydroxybenzoic acid amide, N-(pyridyl-(2)-methyl)-6-chloro-3,5-dinitro-2-isobutyroyloxy-benzoic acid amide, N-(pyridyl-(2)-methyl)-3,5-diamino-2-methyl-benzoic acid amide, N-(pyridyl-(2)-methyl)-6-chloro-2-anilino-3,5-dinitro-benzoic acid amide, N-(pyridyl-(2)-methyl)-2,4-dichloro-3,5-diacetylamino-benzoic acid amide, N-(pyridyl-(3)-methyl)-4-ethylsulphonyl-2-hydroxybenzoic acid amide, N-(pyridyl-(3)-methyl)-2-nitro-4-acetylamino-benzoic acid amide, N-(pyridyl-(3)-methyl)-3-cyano-5-hydroxy-benzoic acid amide, N-(pyridyl-(3)-methyl)-4-butoxycarbonyl-2-ethoxybenzoic acid amide, N-(pyridyl-(4)-methyl)-3-trifluoromethyl-5-dipropylamino-benzoic acid amide, N-(pyridyl-(4)-methyl)-3,5-diacetylamino-2-methyl-benzoic acid amide, N-(pyridyl-(4)-methyl)-2-hydroxy-3-nitro-5-amino-benzoic acid amide, N-(pyridyl-(4)-methyl)-2-chloro-3,5-dipropionylamino-benzoic acid amide, N-(pyridyl-(4)-methyl)-2-hydroxy-3,5-dicyano-benzoic acid amide, N-(benzoxazolyl-(2)-methyl)-3-amino-5-nitrobenzoic acid amide, N-(isoquinolyl-(1)-methyl)-2-hydroxy-3-nitro-5-cyano-benzoic acid amide, N-(pyrazinyl-(2)-ethyl)-2-carboxy-3-cyano-5-nitro-benzoic acid amide and N-(cinnolyl-(4)-methyl-2-hydroxy)-4-methyl-5-amino-benzoic acid amide.

The antibacterial activity of the compounds according to the invention can be conveniently observed in known in vitro and in vivo models.

For the in vitro experiments, Kirchner synthetic nutrient medium - Oxoid complete nutrient medium (nahrboden und Chemie GmbH Wesel) can be used. The active compounds were added to the medium in predetermined concentration gradations of 100 mcg/ml, decreasing with a dilution factor of 2. The culture test tubes were inoculated with the international test strain *Mycobacterium tuberculosis* strain H37Rv and with other *M. tuberculosis* strains isolated from material from patients and exhibiting different degrees of resistance to agents against tuberculosis. In order to define the intensity of the antibacterial action, the action against so-called atypical mycobacteria, Runyon group I to IV, was also tested.

The active compounds according to the invention have the same intensity of action against chemoresistant mycobacteria as against the normally sensitive test strain *M tuberculosis* H37Rv. It follows from this that there is no parallel resistance to chemoresistant mycobacteria. Furthermore, it is possible to conclude that the active compounds according to the invention act on mycobacteria by a different mechanism of action to that of commercially available antituberculosis agents. As a result, the active compounds according to the invention are of particular importance since having a different behavior from that of known mechanisms of action of anti-tuberculosis agents, they can be used for designing multi-medicament therapy schemes, as is necessary in clinical practice.

In vivo experiments can be conducted in white mice (CFl strain, Wikelmann, Kirchborchen) infected with *Mycobacterium tuberculosis* H37Rv. After intravenous infection with $10^4$ to $10^5$ germ units/mouse, treatment is carried out orally or subcutaneously, over a 2-week period on a once daily basis 5 times per week. At predetermined intervals, 11th, 14th and 17th day after infection, mice from the treatment groups were sacrificed, their spleens were removed and standardized smear preparations were prepared from the homogenate. The tubercle germ content in these was then evaluated by means of fluorescent microscopy. The reduction in the number of germs detectable in the treatment groups, as compared to the infected control group which did not receive chemotherapeutic treatment, is taken as an expression of the chemotherapeutic effect of the particular active compound. If, as a result of very low germ counts, the limit of microscopic detection is reached in the method, the recorded values show a germ reduction of 100% as the best value; correspondingly, if the number of germs of a treatment group is the same as that of the control group, the reduction is 0%; i.e., there is no anti-tuberculosis action.

In addition to the experiments on mice infected with tuberculosis, experiments can be carried out analogously in guinea pigs. In this case, the number of germs is determined in a lung homogenate. The animals were infected subcutaneously intrainguinally with *Mycobacterium tuberculosis* H37Rv and subjected to therapy from the 14th day after infection over a period of 3 weeks, once daily 5 times per week. The number of germs was determined in the 4th, 5th and 6th week after infection.

In the case of experimentally produced tuberculosis in mice, the administration of active compounds according to the invention produced a reduction of over 50 and up to 75% in the number of tuberculosis germs in the short-duration therapy experiment. This action was achieved with twice the dose required in the case of Streptomycin which is highly active.

In the case of experimentally produced tuberculosis in guinea pigs, therapeutic results equivalent to those with Ethambutol were achieved in short-duration therapy on administration of a dose of 25 mg per kg of body weight.

The anti-tuberculosis effectiveness of active compounds according to the invention is shown with the aid of some examples in Tables 1 and 2.

TABLE 1

Anti-tuberculosis action in vitro
Inhibiting action in mcg/ml in Kirchner-Tb medium

|  | Example | | | | | |
|---|---|---|---|---|---|---|
| Mycobacterium | No. 8 | No. 11 | No. 2 | No. 18 | No. 6 | No. 19 |
| M.tuberculosis | 25 | 100 | 50 | 10 | 10 | 3 |
| M.bovis | 50 | 100 | 100 | 50 | 10 | 3 |
| M.tuberculosis INH-res. | 25 | 100 | 100 | 25 | 25 | 6 |
| M.tuberculosis TSC-res. | 25 | 100 | 50 | 10 | 25 | 3 |
| M.tuberculosis CS-res. | 25 | 100 | 50 | 10 | 25 | 3 |
| M.tuberculosis PAS-res. | 25 | 100 | 100 | 25 | 10 | 6 |
| M.tuberculosis SM-res. | 25 | 100 | 50 | 10 | 10 | 6 |
| M.tuberculosis RMP-res. | 25 | 100 | 100 | 50 | 10 | 6 |
| M.tuberculosis KM-res. | 25 | 100 | 100 | 10 | 10 | 3 |
| M.tuberculosis INH/TSC/ETH-res. | 50 | 100 | 100 | 50 | 25 | 6 |
| atypical mycobacteria | 50–>100 | 100–>100 | 50–>100 | 10–>100 | 10–>100 | 3–>100 |

CS = Cycloserin, ETH = Ethionamid, INH = Isoniazid, KM = Kanamycin, PAS = p-aminosalicylic acid, RMP = Rifampicin, SM = Streptomycin, TSC = thiosemicarbazone.

TABLE 2

Anti-tuberculosis action in vivo

Tb experiment in mice

Reduction in number of Tb germs: data in % in relation to the infected control

Dose: 100 mg/kg given once daily, 5 times weekly, 10 times in total.

|  | Example | | | | | |
|---|---|---|---|---|---|---|
|  | No. 8 | No. 9 | No. 3 | No. 11 | No. 18 | No. 13 |
| oral administration | 75 | 45 | 55 | 57 | 41 | 49 |
| subcutaneous administration | 53 | 50 | 55 | 42 | 50 | φ |

Therapy control Isoniazid 1 mg/kg: 81%. Streptomycin 50 mg/kg: 77%.

Tb experiment in guinea pigs

Reduction in number of Tb germs: data in % in relation to the infected control

Dose: 25 mg/kg once daily, 5 times weekly, 10 times in total, administered orally; Streptomycin administered subcutaneously

| Example | | | Isoniazid | Streptomycin | Ethambutol |
|---|---|---|---|---|---|
| No. 3 | No. 11 | No. 1 | 2.5 mg/kg | 50 mg/kg | 25 mg/kg |
| 87 | 90 | 67 | 97 | 99 | 88 |

The new active compounds exhibit a low toxicity and a powerful antimicrobial activity. These properties permit their use as chemotherapeutic active compounds in human medicine and veterinary medicine, especially in the case of domestic animals, for example cows.

At high concentrations, the active compound are also active against a large number of microorganisms, including Gram-positive and Gram-negative bacteria, bacteria-like microorganisms, fungi, protozoa and viruses. The following can be mentioned as examples: Micrococcaceae, such as Staphylococci; Lactobacteriaceae, such as Streptococci; Mycobacteriaceae, such as tubercle bacteria; Enterbacteriaceae, such as Escherichia coli, Klebsiellae and Proteus bacteria; Pseudomonadaceae, such as Aeromonas bacteria; parvobacteriaceae, such as Pasteruellae and Bordetella bacteria; Achromobacteriaceae, such as Alcaligensis faecalis; Bacillacae, such as Bacillus substilus; Mycoplasmae, such as Mycoplasma gallisepticum; fungi, such as Trichophyton and Microsporon.

The list of pathogens is purely illustrative and is in no way to be interpreted as limiting.

The active compounds according to the invention are outstandingly active against mycobacteria, especially against tubercle bacteria. They are therefore suitable for chemotherapy of mycobacterioses in human medicine and veterinary medicine.

Hitherto, no parallel resistance to commercially available agents against tuberculosis has been found with the active compounds according to the invention. As a result of the different mechanism of action which this indicates, the new active compounds offer advantages for the composition (essential in tuberculosis therapy) of combinations of medicaments of specific anti-tuberculosis activity.

The spectrum of action of the compounds according to the invention also embraces so-called "atypical mycobacteria", which increasingly cause mycobacterioses which have hitherto been difficult to treat by chemotherapy.

As stated above, the invention also relates to the use in human and veterinary medicine of the compounds of the invention.

The compounds of the present invention are administered parenterally or orally in any of the usual pharmaceutical forms. These include solid and liquid oral unit dosage forms such as tablets, capsules, powders, suspensions, solutions, syrups and the like, including sustained release preparations, and fluid injectable forms such as sterile solutions and suspensions. The term unit dosage form as used in this specification and the claims refer to physically discrete units to be administered in single or multiple dosage to animals, each unit containing a predetermined quantity of active material in association with the required diluent, carrier or vehicle. The quantity of active material is that calculated to produce the desired therapeutic effect upon administration of one or more of such units.

Powders are prepared by comminuting the compound to a suitable fine size and mixing with a similarly comminuted diluent pharmaceutical carrier such as an edible carbohydrate material as for example, starch. Sweetening, flavoring, preservative, dispersing and coloring agents can also be present.

Capsules are made by preparing a powder mixture as described above and filling formed gelatin sheaths. A lubricant such as talc, magnesium stearate and calcium stearate can be added to the powder mixture as an adjuvant before the filling operation; a glidant such as colloidal silica may be added to improve flow properties; a disintegrating or solubilizing agent may be added to improve the availability of the medicament when the capsule is ingested.

Tablets are made by preparing a powder mixture, granulating or slugging, adding a lubricant and disintegrant and pressing into tablets. A powder mixture is prepared by mixing the compound, suitably comminuted, with a diluent or base such as starch, sucrose, kaolin, dicalcium phosphate and the like. The powder mixture can be granulated by wetting with a binder such as syrup, starch paste, acacia mucilege or solution of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A protective coating consisting of a sealing coat of shellac, a coating of sugar or polymeric material and a polish coating of wax can be provided. Dyestuffs can be added to these coatings to distinguish different unit dosages.

Oral fluids such as syrups and elixirs can be prepared in unit dosage form so that a given quantity, e.g., a teaspoonful, contains a predetermined amount of the compound. Syrups can be prepared by dissolving the compound in a suitably flavored aqueous sucrose solution while elixirs are prepared through the use of a non-toxic alcoholic vehicle. Suspensions can be formulated by dispersing the compound in a non-toxic vehicle in which it is insoluble.

Fluid unit dosage forms for parenteral administration can be prepared by suspending or dissolving a measured amount of the compound in a non-toxic liquid vehicle suitable for injection such as an aqueous or oleaginous medium and sterilizing the suspension or solution. Alternatively a measured amount of the compound is placed in a vial and the vial and its contents are sterilized and sealed. An accompanying vial or vehicle can be provided for mixing prior to administration.

In general satisfactory antibacterial effects are obtained when the compounds are administered in doses of from about 20 mg to about 200, preferably 30 to 100, mg/kg of body weight per day. An individual administration preferably contains an active compound according to the invention in an amount of from 6.5 to 60, preferably 10 to 33 mg/kg of body weight. Nevertheless, it will at times be necessary to deviate from those dosage rates, and in particular to do so as a function of the nature and body weight of the animal being treated, the individual reaction of this subject to the treatment, the type of formulation in which the active ingredient is administered and the mode in which the administration is carried out, and the point in the progress of the disease or interval at which it is to be administered. Thus it may in some case suffice to use less than the above-mentioned minimum dosage rate, while in other cases the upper limit mentioned must be exceeded to achieve the desired results. Where larger amounts are administered it can be advisable to divide these into several individual administrations over the course of the day.

The following examples will serve to further illustrate the nature of the invention without being a limitation on the scope thereof, the scope being defined solely by the appended claims.

EXAMPLE 1

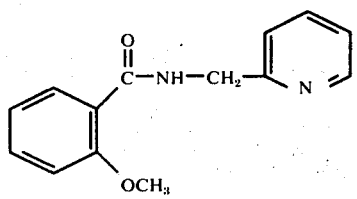

A solution of 34 g of 2-methoxybenzoyl chloride in 200 ml of toluene is added to a solution of 25 g of α-aminomethylpyridine, 30 ml of treithylamine and 100 ml of toluene over the course of 10 minutes at 15° to 20° C (ice bath). The mixture is stirred for a further 4 hours at room temperature, 400 ml of half-concentrated sodium carbonate solution are added, and this mixture is stirred for a further hour and extracted twice with toluene. After drying and concentrating the organic phase, 34 g (70% of theory) of N-[pyridyl-(2)-methyl]-2-methoxy-benzoic acid amide of boiling point 180 to 190° C/0.05 mm Hg are obtained.

EXAMPLE 2

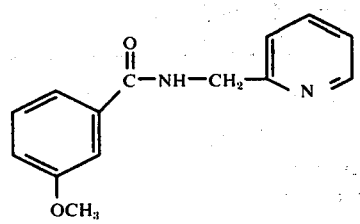

8.8 g of dicyclohexylcarbodiimide are added to a solution of 6.8 g of 3-methoxybenzoic acid in 60 ml of toluene. 4.8 g of α-aminomethylpyridine are then added, the mixture is stirred for one day at room temperature, and the dicyclohexylurea which has precipitated is filtered off. The mother liquor is concentrated and the residue is recrystallised from toluene. 7.5 g (42%) of N-[pyridyl-(2)-methyl]-3-methoxybenzoic acid amide of melting point 52° to 53° C are thus obtained.

EXAMPLE 3

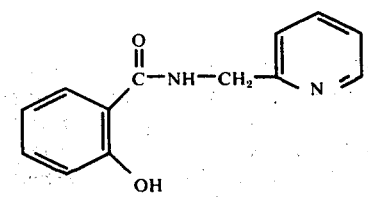

30.4 g of 2-hydroxy-benzoic acid methyl ester and 25 g of 2-aminomethylpyridine are heated to 125° C for 4 hours. After having cooled, the product is recrystallised from toluene. 23 g (51% of theory) of N-[pyridyl-(2)- methyl]-2-hydroxybenzoic acid amide of melting point 116° to 118° C are thus obtained.

EXAMPLE 4

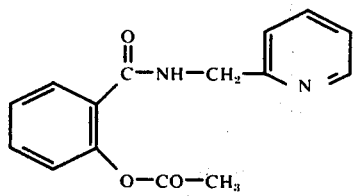

23 g of the reaction product from Example 3 and 11 g of acetic anhydride are heated to 80° C for 4 hours. The solvent is distilled off in vacuo and ether is added to the oily residue. Hereupon 22 g (81.5% of theory) of N-[pyridyl-(2)-methyl]-2-acetoxy-benzamide crystallise out. Melting point 87° to 88° C (88° to 89° C after recrystallisation from carbon tetrachloride).

EXAMPLE 5

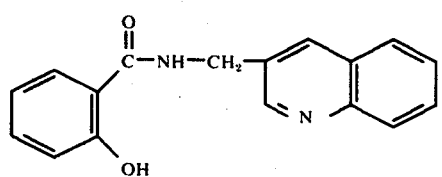

15.8 g of 3-aminomethylquinoline are added to a solution of 21.4 g of salicylic acid phenyl ester in 80 ml of toluene (an exothermic effect ensues and the temperature rises to 33+ C). After 20 hours, the precipitate which has separated out is filtered off with ether and dried. Yield: 18 g (64% of theory; melting point 213° to 215° C) of N-[quinolyl-(3)-methyl]-2-hydroxybenzoic acid amide.

EXAMPLE 6

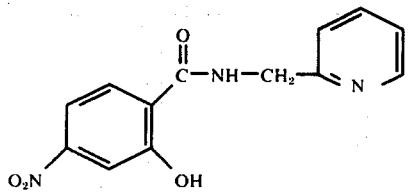

39.4 g of 4-nitro-2-hydroxy-benzoic acid methyl ester and 21.6 g of 2-aminomethylpyridine are heated to 120° C, in the course of which methanol distils off. After approx. 30 minutes, the reaction mixture solidifies. It is allowed to cool to 50° C and is recrystallised from methanol. 28.5 g (52% of theory) of N-[pyridyl-(2)-methyl]-2-hydroxy-4-nitrobenzamide of melting point 185° to 186° are obtained.

EXAMPLE 7

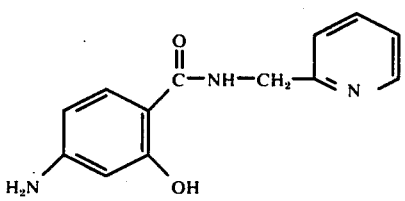

28.5 g of the reaction product from Example 6 in 170 ml of tetrahydrofurane are hydrogenated in the presence of 5 g of Raney nickel at 30° C under a $H_2$ pressure of 50 bars. An amount of $H_2$ equivalent to a pressure drop of 64 bars was absorbed over the course of 5 hours. After filtering off the catalyst, the solution was evaporated in vacuo, the residue was dissolved in methanol, the solution was filtered through charcoal and water was added to the filtrate. Hereupon 15 g (60% of theory) of N-[pyridyl-(2)-methyl]-2-hydroxy-4-aminobenzamide of melting point 183° to 185° C crystallised out. The melting point of a mixture with the reaction product from Example 6 is 171° to 177° C.

Further amides of the formula I prepared in accordance with the invention are listed in the table which follows:

Table

| Example No. | R | R¹ | R² | R³ | R⁴ | A |
|---|---|---|---|---|---|---|
| 8 | H | 4-CH₃O | H | H | H | —CH₂— |
| 9 | H | 4-CH₃O | 3-NO₂ | H | H | —CH₂— |
| 10 | H | 2-NH₂ | H | H | H | —CH₂— |
| 11 | H | 4-OH | H | H | H | —CH₂— |
| 12 | H | 3-CH₃O | 4-CH₃O | 5-CH₃O | H | —CH₂— |
| 13 | H | 3-OH | H | H | H | —CH₂— |
| 14 | H | 3-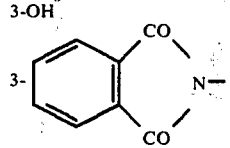 | 5-NO₂ | H | H | —CH₂— |
| 15 | H | 2-OH | H | H | H | —CH₂— |

Table-continued

| | | | | | | |
|---|---|---|---|---|---|---|
| 16 | H | 2-OH | H | H | H | $-CH_2-$ |
| 17 | H | 2-OH | H | H | H | $-CH_2-$ |
| 18 | H | 2-OH | 5-Cl | H | H | $-CH_2-$ |
| 19 | H | 2-OH | 5-NO$_2$ | H | H | $-CH_2-$ |
| 20 | H | 2-OH | 3-NO$_2$ | 5-NO$_2$ | H | $-CH_2-$ |
| 21 | H | 2-OH | 3-CH$_3$ | H | H | $-CH_2-$ |
| 22 | H | 4-OH | H | H | H | $-CH_2-$ |
| 23 | H | 2-OH | H | H | H | $-CH_2-$ |
| 24 | H | 3-NH$_2$ | 5-NH$_2$ | H | H | $-CH_2-$ |
| 25 | H | 3-NH—CO—CH$_3$ | 5-NH—CO—CH$_3$ | H | H | $-CH_2-$ |
| 26 | H | 3-NH-COOC$_2$H$_5$ | 5-NH-COOC$_2$H$_5$ | H | H | $-CH_2-$ |
| 27 | H | 2-OH | H | H | H | $-CH(CH_3)-$ |
| 28 | H | 2-OH | H | H | H | $-CH_2-$ |
| 29 | H | 2-OH | H | H | H | $-CH_2-$ |
| 30 | H | 4-OH | 5-NH$_2$ | H | H | $-CH_2-$ |
| 31 | benzyl (PhCH$_2$-) | 4-OH | H | H | H | $-CH_2-$ |
| 32 | 2-pyridyl-CH$_2-$ | 4-OH | H | H | H | $-CH(C_6H_5)-$ |
| 33 | H | 4-O—CO—CH$_3$ | H | H | H | $-CH_2-CH_2-$ |
| 34 | H | 2-OH | 5-Cl | H | H | $-CH_2-CH_2-CH_2-$ |
| 35 | H | 3-NH$_2$ | 5-CN | H | H | $-CH_2-CH_2-CH_2-$ |
| 36 | H | 3-NH$_2$ | 5-NO$_2$ | H | H | $-CH_2-$ |
| 37 | H | 4-n-C$_4$H$_9$O | H | H | H | $-CH_2-$ |
| 38 | H | 2-OH | 5-(CH$_3$)$_3$C | H | H | $-CH_2-$ |
| 39 | H | 4-CH$_3$O | H | H | H | $-CH_2-$ |
| 40 | H | 2-OH | 5-Cl | H | H | $-CH_2-$ |
| 41 | H | 3-Cl | 4-OH | H | H | $-CH_2-$ |
| 42 | H | 2-OH | 3-CH$_3$ | 5-Cl | H | $-CH_2-$ |
| 43 | H | 2-OH | 4-CH$_3$O | H | H | $-CH_2-$ |
| 44 | H | 3-NH$_2$ | 4-CH$_3$O | H | H | $-CH_2-$ |
| 45 | H | 3-O—CO—CH$_3$ | 4-O—CO—CH$_3$ | 5-O—CO—CH$_3$ | H | $-CH_2-$ |
| 46 | CH$_3$ | 2-OH | H | H | H | $-CH_2-$ |

| Example No. | Het | Yield (% of theory) | Melting point |
|---|---|---|---|
| 8 | 2-pyridyl | 87 % | 154 – 155° |
| 9 | 2-pyridyl | 55 % | 149 – 151° |
| 10 | 2-pyridyl | 57 % | 133 – 134° |
| 11 | 2-pyridyl | 30 % | 180 – 181° |
| 12 | 2-pyridyl | 91 % | 110 – 112° |
| 13 | 2-pyridyl | 62 % | 177 – 178° |
| 14 | 2-pyridyl | 51 % | 168 – 170° |

Table-continued
| | | | |
|---|---|---|---|
| 15 | 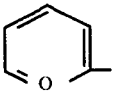 | 77 % | 45 – 46° |
| 16 | 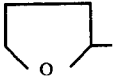 | 71 % | B.p. 165°/0.05 |
| 17 | 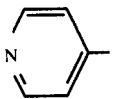 | 66 % | 127 – 129° |
| 18 | 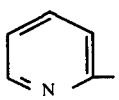 | 72 % | 158 – 160° |
| 19 | 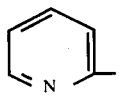 | 35 % | 211 – 212° |
| 20 | 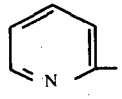 | 68 % | 255 – 256° Decomposition |
| 21 | 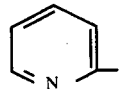 | 40% | 140 – 142° |
| 22 | 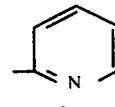 | 84 % | 121 – 122° |
| 23 | 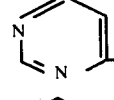 | 59 % | 112 – 114° |
| 24 | 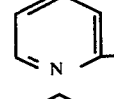 | 50 % | 185 – 186° |
| 25 | 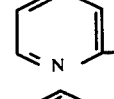 | 92 % | 199 – 200° |
| 26 | 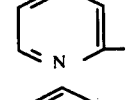 | 67 % | 189 – 190° |
| 27 | 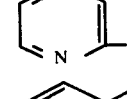 | 43 % | 127° |
| 28 | 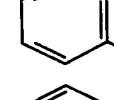 | 54 % | 157 – 159° |
| 29 | 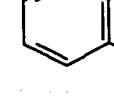 | 68 % | 151 – 153° |
| 30 | 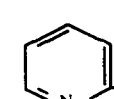 | 45 % | 113 – 116° |
| 31 | 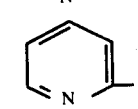 | 48 % | 70 – 72° |

Table-continued

| # | Structure | Yield | m.p. |
|---|---|---|---|
| 32 | pyridine | 65 % | 165 – 167° |
| 33 | pyrazine | 59 % | 122 – 124° |
| 34 | N-methylpyrrole | 72 % | 95 – 97° |
| 35 | 7-chloro-1-methylindazole | 61 % | 124 – 125° |
| 36 | pyridine | 80 % | 164 – 165° |
| 37 | pyridine | 72 % | 96 – 98° |
| 38 | pyridine | 50 % | 132 – 134° |
| 39 | pyridine | 82 % | 78 – 80° |
| 40 | pyridine | 69 % | 169 – 172° |
| 41 | pyridine | 70 % | 178 – 180° |
| 42 | pyridine | 63 % | 164 – 166° |
| 43 | pyridine | 86 % | 119 – 122° |
| 44 | pyridine | 83 % | 169 – 170° |
| 45 | pyridine | 80 % | 125 – 127° |
| 46 | pyridine | 58 % | 106 – 108° |

What is claimed is:

1. The method of combatting systemic Mycobacterium infections in humans and other animals which comprises administering parenterally or orally to said human or animal from about 20 to about 200 mg/kg of body weight daily of a compound of the formula:

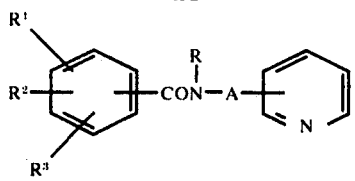

wherein A is methylene, ethylene, propylene or benzylidene;

R is hydrogen, methyl, benzyl or pyridylmethyl; and
each of $R^1$, $R^2$ and $R^3$ is selected from the group consisting of hydrogen, hydroxy, alkoxy of 1 to 4 carbon atoms, alkanoyloxy of 2 to 4 carbon atoms, amino, alkanoylamido of 2 to 4 carbon atoms, carbalkoxyamido of 3 to 5 carbon atoms, chloro, bromo, alkyl of 1 to 4 carbon atoms, nitro, trifluoromethyl and cyano provided that one of $R^1$, $R^2$ and $R^3$ is hydroxy, alkoxy, alkanoyloxy, amino, alkanoylamido or carbalkoxyamido.

2. The method according to claim 1 wherein R is hydrogen, methyl, ethyl, benzyl or pyridylmethyl.

3. The method according to claim 1 wherein A is methylene, ethylene, propylene or benzylidene.

4. The method according to claim 1 wherein one of $R^1$, $R^2$ and $R^3$ in said compound is hydroxy, alkoxy of 1 to 4 carbon atoms or amino.

5. The method according to claim 1 wherein said compound is administered in a pharmaceutical composition in combination with a pharmaceutical carrier.

6. The method according to claim 1 wherein said compound is N-[pyridyl-(2)-methyl]-3-methoxybenzoic acid amide.

7. The method according to claim 1 wherein said compound is N-[pyridyl-(2)-methyl]-2-hydroxybenzoic acid amide.

8. The method according to claim 1 wherein said compound is N-[pyridyl-(2)-methyl]-2-hydroxy-4-nitrobenzoic acid amide.

9. The method according to claim 1 wherein said compound is N-[pyridyl-(2)-methyl-]4-methoxybenzoic acid amide.

10. The method according to claim 1 wherein said compound is N-[pyridyl-(2)-methyl]-3-nitro-4-methoxybenzoic acid amide.

11. The method according to claim 1 wherein said compound is N-[pyridyl-(2)-methyl]-4-hydroxybenzoic acid amide.

12. The method according to claim 1 wherein said compound is N-[pyridyl-(2)-methyl]-3-hydroxybenzoic acid amide.

13. The method according to claim 1 wherein said compound is N-[pyridyl-(2)-methyl]-2-hydroxy-5-chlorobenzoic acid amide.

14. The method according to claim 1 wherein said compound is N-[pyridyl-(2)-methyl]-2-hydroxy-5-nitrobenzoic acid amide.

* * * * *